US008144001B1

(12) United States Patent
D'Souza

(10) Patent No.: US 8,144,001 B1
(45) Date of Patent: Mar. 27, 2012

(54) VIBRATIONAL AWAKENING APPARATUS

(76) Inventor: Adrian J. D'Souza, Queens Village, NY (US)

( * ) Notice: Subject to any disclaimer, the term of this patent is extended or adjusted under 35 U.S.C. 154(b) by 237 days.

(21) Appl. No.: 12/247,167

(22) Filed: Oct. 7, 2008

(51) Int. Cl.
   *B60Q 1/00* (2006.01)
(52) U.S. Cl. .................................. 340/435; 340/573.1
(58) Field of Classification Search .................. 340/435, 340/573.1, 539.12
   See application file for complete search history.

(56) References Cited

U.S. PATENT DOCUMENTS

| | | | |
|---|---|---|---|
| 3,955,222 A | 5/1976 | Pater | |
| D285,608 S | 9/1986 | Rauch | |
| 5,076,260 A | 12/1991 | Komatsu | |
| 6,236,621 B1 | 5/2001 | Schettino | |
| 6,421,235 B2 * | 7/2002 | Ditzik | 361/679.3 |
| 6,502,264 B1 | 1/2003 | Clothier et al. | |
| 2005/0159685 A1 | 7/2005 | Klein et al. | |
| 2007/0060015 A1 * | 3/2007 | Glatt et al. | 446/227 |
| 2007/0096927 A1 * | 5/2007 | Albert | 340/573.1 |
| 2007/0289060 A1 * | 12/2007 | Berkey | 5/99.1 |
| 2010/0000020 A1 * | 1/2010 | Poulos | 5/713 |

* cited by examiner

*Primary Examiner* — Shirley Lu

(57) ABSTRACT

The vibrational awakening apparatus provides a pad of resilient material for selective placement and securement atop an existing mattress. The pad contains a plurality of equidistantly spaced apart vibrators and sensors dispersed throughout the resilient material. The controller for the pad is in communication with the vibrators and the sensors. The components of controller in communication are the clock with clock controls, the vibrator control, the buzzer control, the off control, the combined vibrator/buzzer control, and the speaker in communication with the buzzer control. A user can choose vibration only or a combination of vibration and buzzer for awakening. The awakening functions do not turn off until the sensors sense an absence of the user atop the pad.

5 Claims, 5 Drawing Sheets

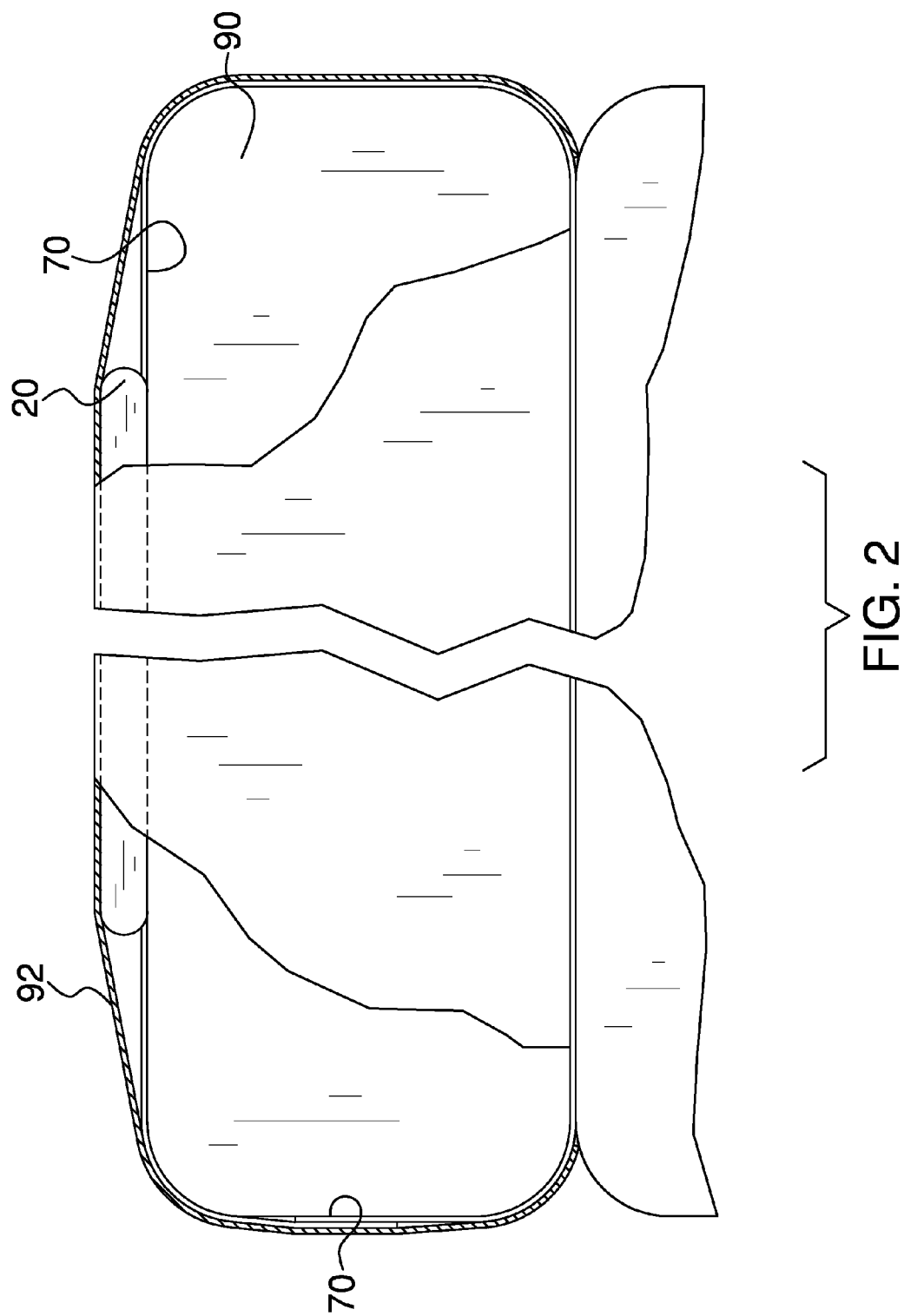

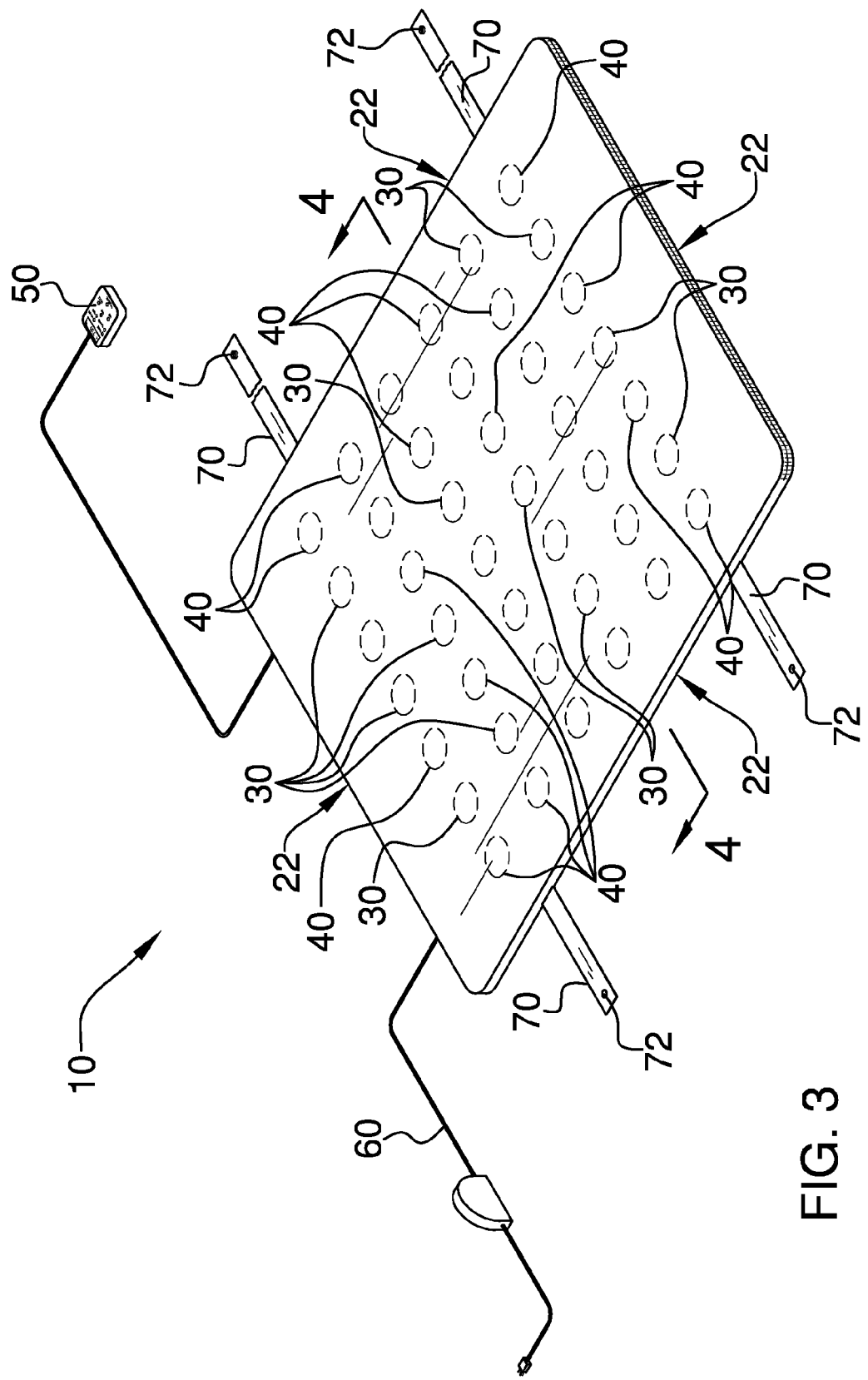

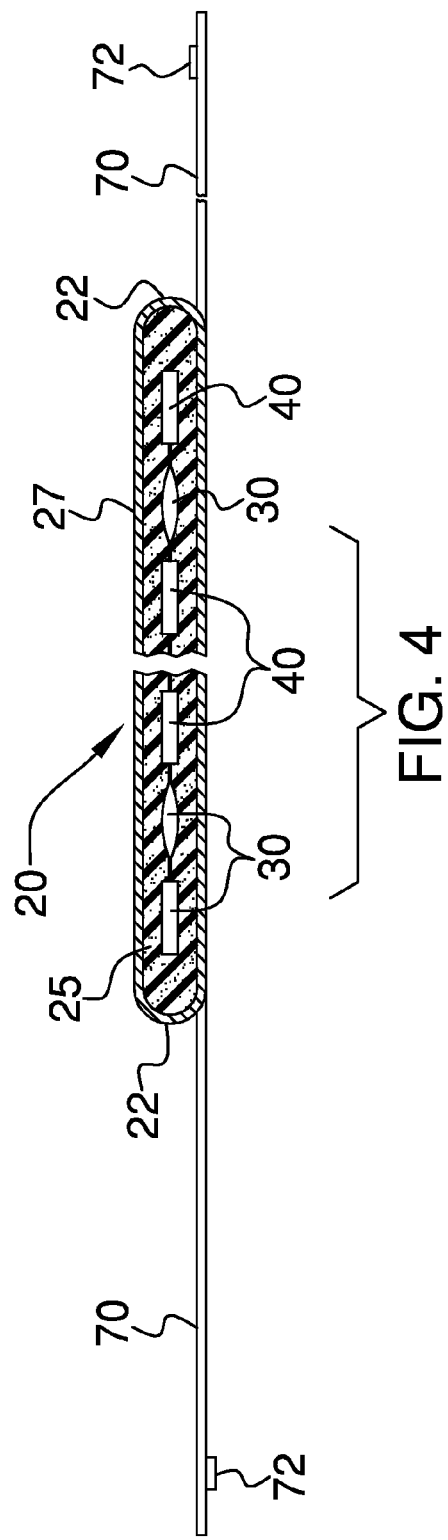
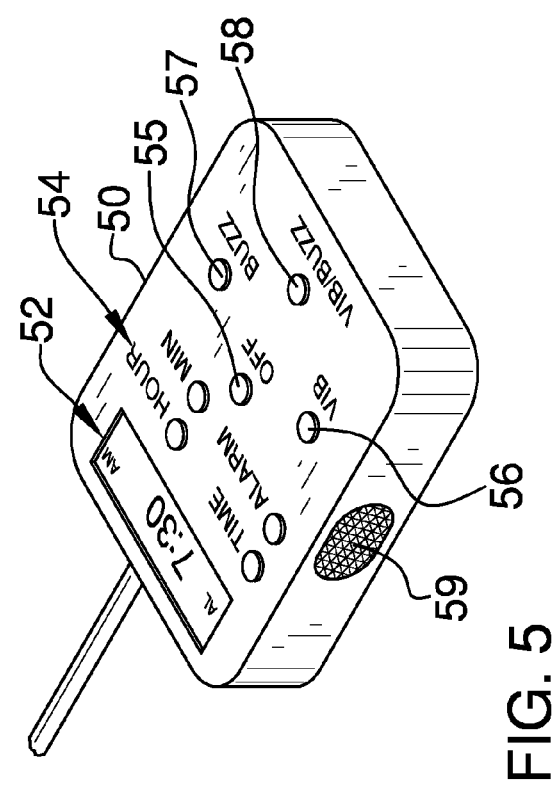

VIBRATIONAL AWAKENING APPARATUS

BACKGROUND OF THE INVENTION

Various devices for awakening a person are known, as are awakening devices which use vibration to awake a sleeping person. Such devices are usually set as is an alarm clock, and typically operate for a set period of time prior to turning off, or require a sleeping person to switch off operation. One problem with allowing a person to switch off an awakening device is well known. A sleeping person, especially one who is difficult to awake, often simply leans over and switches off whatever awakening mechanism is employed, and then falls back asleep. The means for switching off an awakening alarm are therefore crucial to many with regard to awakening success. A further problem with many vibrational devices used for awakening a person is that many such devices are localized, such as a pillow, for example. A localized device can be either moved or moved away from, allowing the sleeping person to remain asleep or return to sleep.

Vibrating devices which attach to a bed frame or headboard have not always been successful because retrofit to an existing bed can produce vibrations which are destructive to the integrity of the bed. Vibration devices which are incorporated into a bed from the outset of production require structural integrity of the bed which significantly increases the expense of production and sale. Additionally, devices which incorporate only one means of awakening a person can fail, given a person who is prone to continued sleep without more than one awakening stimulus. What has been needed is an apparatus for awakening a sleeping person which can be set to initiate an awakening means, or more than one awakening means and continues the awakening means until the sleeping person is no longer present upon the sleep surface. The apparatus must avoid the above pitfalls in order to be fully effective. The present apparatus provides these solutions.

FIELD OF THE INVENTION

The vibrational awakening apparatus relates to alarm devices for awakening a sleeping person and more especially to an alarm apparatus for awakening a sleeping person by vibration, sound, or both, and switches off only with the person absent from the sleeping surface.

SUMMARY OF THE INVENTION

The general purpose of the vibrational awakening apparatus, described subsequently in greater detail, is to provide a vibrational awakening apparatus which has many novel features that result in an improved vibrational awakening apparatus which is not anticipated, rendered obvious, suggested, or even implied by prior art, either alone or in combination thereof.

To attain this, the vibrational awakening apparatus provides a means of awakening a sleeping person with or without an audio alarm. The apparatus features a pad which is placed atop any bed, the pad offered in a variety of sizes. The pad is selectively fastened via the fasteners on the straps which are provided on each side of the pad. The straps are of sufficient length to surround an existing bed mattress. The apparatus combines the selective choice of vibration with or without the use of an audio alarm in the controller. Vibrators are evenly dispersed throughout the resilient material of the pad. The pad cover, for sanitization purposes, can be removed from the resilient material. Also in the pad, importantly, are the sensors which also are evenly dispersed among themselves and among the vibrators, alternately. The sensors can be temperature or pressure or other types of sensors used to sense the presence of a person on the bed. The ideal choice is pressure sensors which detect the presence or lack thereof of a person lying atop the pad.

Whether an individual dislikes the use of an alarm, or even if an alarm fails to wake a sleeper, the apparatus offers the alternative of vibration that is automatically switched off when the pressure sensors sense the lack of a person atop the pad. The vibration strength of the vibrators can be sequentially increased by repeated vibrator control press. Therefore, a user can tailor the strength of vibration. Thus has been broadly outlined the more important features of the improved vibrational awakening apparatus so that the detailed description thereof that follows may be better understood and in order that the present contribution to the art may be better appreciated.

An object of the vibrational awakening apparatus is to awaken a sleeping person by more than one means, selectively.

Another object of the vibrational awakening apparatus is to awaken a sleeping person via vibration.

A further object of the vibrational awakening apparatus is to awaken a sleeping person via vibration and sound.

An added object of the vibrational awakening apparatus is to continue an awakening function until the person is no longer present upon a sleeping surface.

And, an object of the vibrational awakening apparatus is to provide for fully awakening a sleeping person with a cost effective apparatus which can be easily fitted to and removed from a variety of sleeping surfaces.

These together with additional objects, features and advantages of the improved vibrational awakening apparatus will be readily apparent to those of ordinary skill in the art upon reading the following detailed description of presently preferred, but nonetheless illustrative, embodiments of the improved vibrational awakening apparatus when taken in conjunction with the accompanying drawings.

In this respect, before explaining the current embodiments of the improved vibrational awakening apparatus in detail, it is to be understood that the vibrational awakening apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved vibrational awakening apparatus. It is therefore important that the claims be regarded as including such equivalent constructions insofar as they do not depart from the spirit and scope of the vibrational awakening apparatus. It is also to be understood that the phraseology and terminology employed herein are for purposes of description and should not be regarded as limiting.

BRIEF DESCRIPTION OF THE DRAWINGS

FIG. 2 is a partial cross sectional view of the pad of the apparatus fitted to a bed.

FIG. 3 is a perspective view.

FIG. 4 is a partial cross sectional view of FIG. 3.

FIG. 5 is a perspective view of the controller.

DETAILED DESCRIPTION OF THE DRAWINGS

Figure 1:
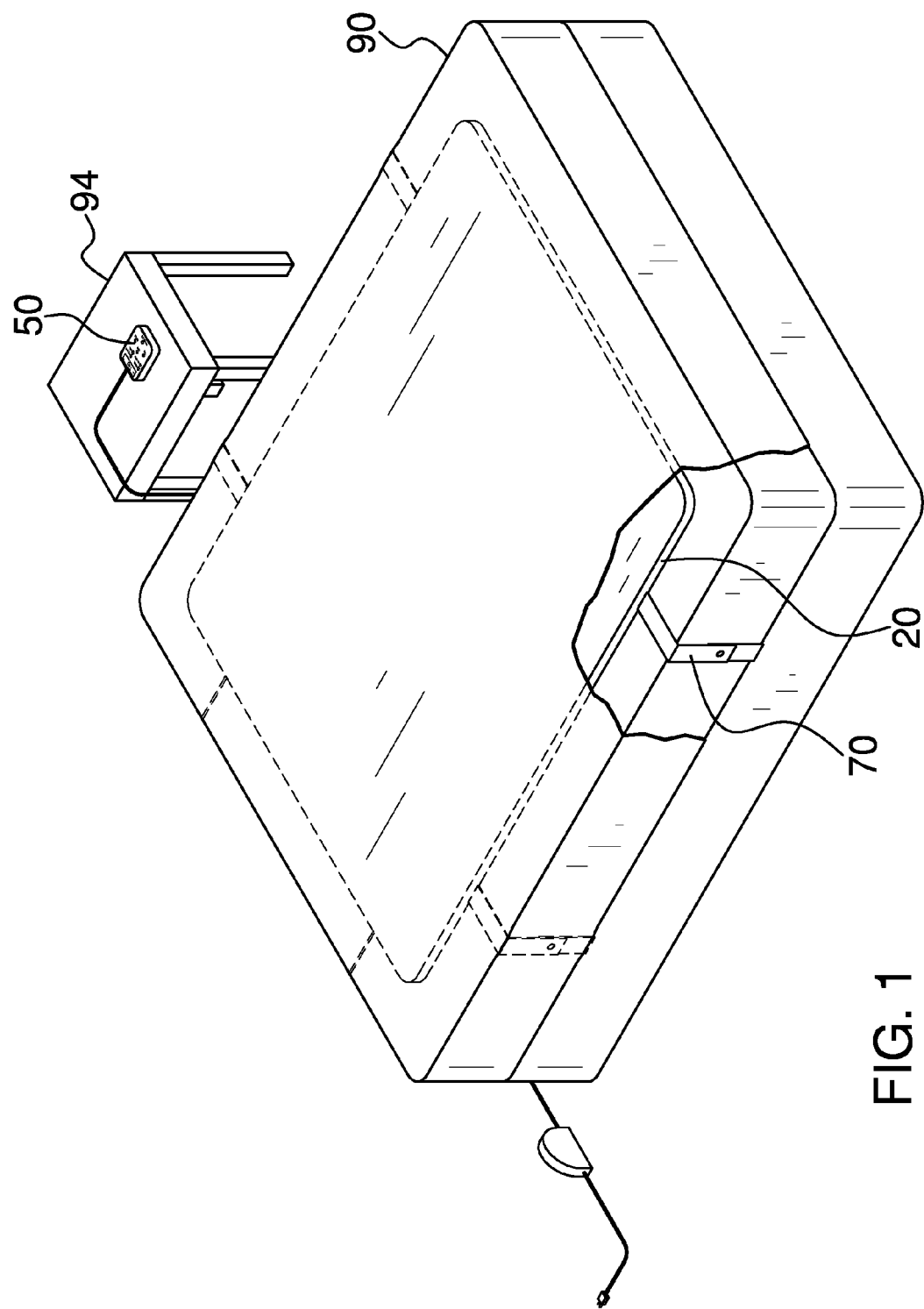
FIG. 1 is a perspective view of the apparatus fitted to a bed.

With reference now to the drawings, and in particular FIGS. 1 through 6 thereof, the principles and concepts of the vibrational awakening apparatus generally designated by the reference number 10 will be described.

Referring to FIGS. 1-5, the vibrational awakening apparatus 10 is partially comprises the rectangular mattress pad 20 selectively disposed atop an existing mattress 90. The pad 20 has a quartet of spaced apart sides 22. The pad 20 further comprises a removable cover 27 disposed around the pad 20. A resilient material 25 is disposed within the cover 27. A plurality of equidistantly spaced apart vibrators 40 is dispersed throughout the resilient material 25. A plurality of equidistantly spaced apart sensors 30 is evenly dispersed throughout the resilient material 25. The sensors 30 are evenly dispersed among the vibrators 40. Two pair of spaced apart straps 70 with fasteners 72 are extended from two of the pad sides 22. Each pair of straps 70 is selectively fastened. The controller 50 is provided for the pad 20. The controller 50 is in communication with the vibrators 40 and the sensors 30. The sensors 30 are pressure sensor discs and the vibrators 40 are vibrating discs.

The controller 50 partially comprises the clock 52 with clock controls 54. The clock controls 54 allow a user to set the time that the chosen functions of the controller 50 occur. The controller 50 further comprises the vibrator control 56 which allow a user to arm or disarm the vibrators 40. The controller 50 comprises the buzzer control 57 which allows a user to arm or disarm a buzzer (not shown) within the controller 50 which is in communication with the speaker 59. The off control 55 allows a user to totally turn the apparatus 10 off. While the illustration shows the table 94 proximal to the mattress 90, this is for the purpose of space utilization only on the illustration. Ideally, the controller 50 with or without existing table 94 is positioned such that a user must get up from the apparatus 10 to operate the controller 50. Ideally, an existing sheet 92 is placed over the pad 20. The combined vibrator/buzzer control 58 allows a user to selectively choose both vibrators 40 and buzzer. The power cord with retractor 60 is in communication with the controller 50.

Figure 6:
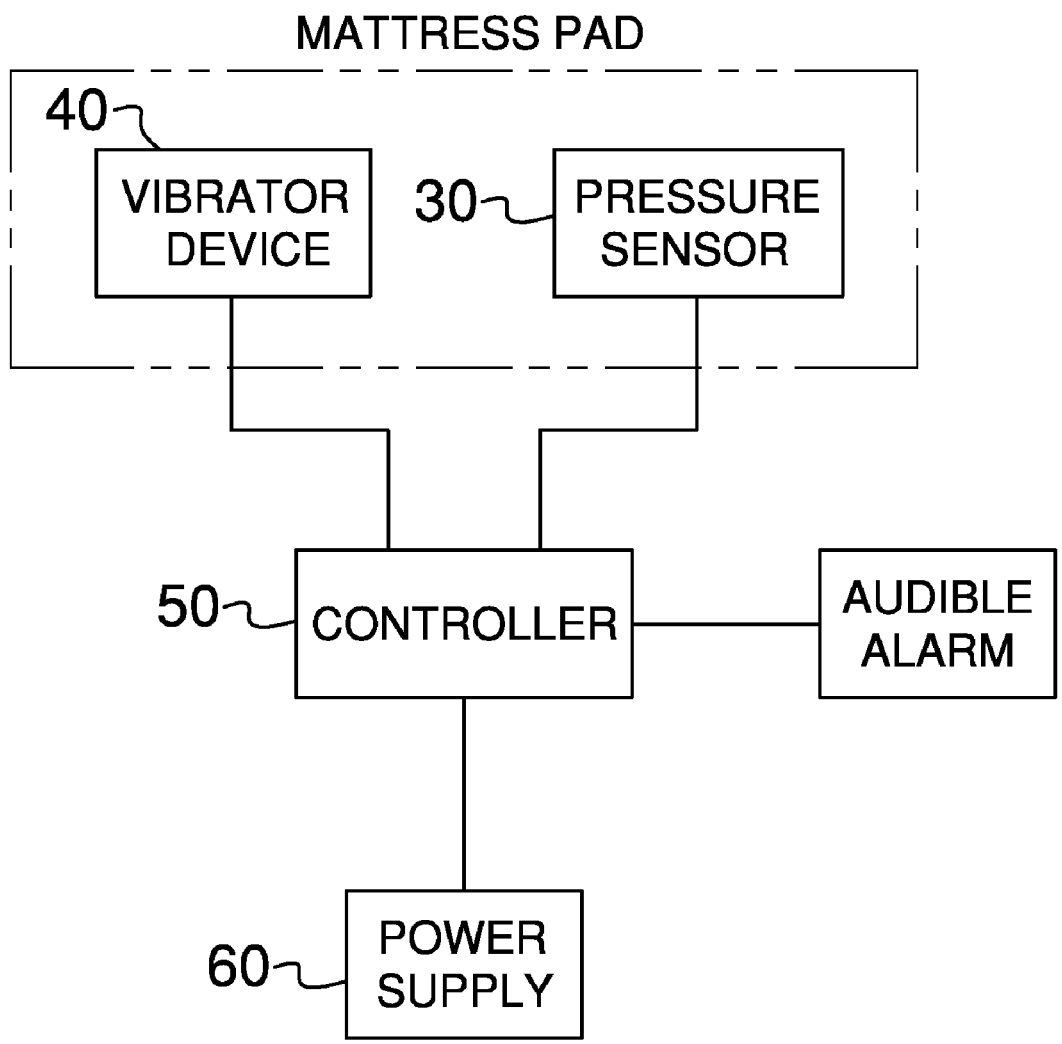
FIG. 6 is a schematic block diagram of the communication between the electronic components of the apparatus.

Referring to FIG. 6, with the power supply 60 plugged into an existing outlet, a user can select to turn the apparatus 10 on. The user then chooses the appropriate above listed control feature, for example, the combined vibrator/buzzer control 58. The time for alarm is set via the clock controls 54. The user sleeps until the set time whereupon the audio alarm is issued automatically via the speaker 59. Also, the vibrators 40 vibrate, at the set strength. The vibrators 40 and buzzer sounds do not cease until the sensors 30 detect an absence of the user upon the pad 20.

With respect to the above description then, it is to be realized that the optimum dimensional relationships for the parts of the vibrational awakening apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the vibrational awakening apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the vibrational awakening apparatus may be used.

Therefore, the foregoing is considered as illustrative only of the principles of the vibrational awakening apparatus. Further, since numerous modifications and changes will readily occur to those skilled in the art, it is not desired to limit the vibrational awakening apparatus to the exact construction and operation shown and described, and accordingly, all suitable modifications and equivalents may be resorted to, falling within the scope of the vibrational awakening apparatus.

What is claimed is:

1. A vibrational awakening comprising:
   a rectangular mattress pad selectively disposed atop an existing mattress, the pad having a quartet of spaced apart sides, the pad further comprising:
   a removable cover disposed around the pad;
   a resilient material within the cover;
   a plurality of equidistantly spaced apart vibrating discs dispersed throughout the resilient material;
   a plurality of equidistantly spaced apart pressure sensor discs dispersed throughout the resilient material, the sensors evenly dispersed among the vibrators, sensing a presence of a human upon the pad;
   at least a pair of spaced apart straps with fasteners extended from two of the pad sides, each pair selectively fastened;
   a controller for the pad, the controller in communication with the vibration means and the sensing means, the controller comprising:
   a clock with clock controls;
   a sequential vibration means control;
   a buzzer control;
   a speaker in communication with the buzzer control;
   an off control;
   a combined vibration means and buzzer control;
   a power cord with retractor in communication with the controller; wherein the pad cover is further removable;
   wherein the vibration means further comprises a plurality of spaced apart vibrating discs within the pad.

2. The apparatus according to claim 1 wherein the sensing means further comprises means for sensing a pressure upon the pad.

3. The apparatus according to claim 2 wherein the sensing means further comprises means for sensing a pressure upon the pad.

4. The apparatus according to claim 2 wherein the sensing means further comprises means for sensing a pressure upon the pad.

5. The apparatus according to claim 4 wherein the sensing means further comprises means for sensing a pressure upon the pad.

\* \* \* \* \*